(12) United States Patent
Souluer

(10) Patent No.: US 6,192,143 B1
(45) Date of Patent: Feb. 20, 2001

(54) APPARATUS FOR DETECTING VERY SMALL BREAST ANOMALIES

(75) Inventor: Farid Souluer, Exton, PA (US)

(73) Assignee: UltraTouch Corporation, Paoli, PA (US)

(*) Notice: Under 35 U.S.C. 154(b), the term of this patent shall be extended for 0 days.

(21) Appl. No.: 08/957,648

(22) Filed: Oct. 24, 1997

(51) Int. Cl.[7] .................................................. A61B 10/00
(52) U.S. Cl. .............................................. 382/128; 600/587
(58) Field of Search .................................... 382/128, 325; 128/915, 920; 378/37; 600/550, 587; 33/511

(56) References Cited

U.S. PATENT DOCUMENTS

| | | | |
|---|---|---|---|
| 5,524,636 | * 6/1996 | Sarvazyan et al. | 128/774 |
| 5,833,633 | * 11/1998 | Sarvazyan | 600/587 |
| 5,833,634 | * 11/1998 | Laird et al. | 600/587 |
| 5,860,934 | * 1/1999 | Sarvazyan | 600/587 |
| 5,879,312 | * 3/1999 | Imoto | 600/587 |

OTHER PUBLICATIONS

Sarvazyan et al., "Mechanical Introscopy—A New Modality of Medical Imaging for Detection of Breast and Prostate Cancer," *Proc. of the 8th IEEE Symposium on Computer-Based Medical Systems*, Jun. 9–10 1995, pp. 4–5.*

* cited by examiner

*Primary Examiner*—Andrew W. Johns
(74) *Attorney, Agent, or Firm*—Alfred W. Zaher, Esq.; Saul Ewing Remick & Saul, LLP

(57) ABSTRACT

A computer controlled apparatus for detecting breast tumors by mechanically palpating in a full surface scan manner to detect even very small lumps or other anomalies. The patient is positioned on a fully adjustable bed and oriented relative the apparatus. A detection head mounted for movement in three dimensions is positioned above the bed. A palpation finger is brought into pressure contact with a sequence of small areas across the entire breast, palpating each area to measure tissue density. Concurrent with the palpation scan, a scan of breast color and temperature is conducted. A locator head positions the detector for the scan in a manner that assures repeatability of the palpation scan during each of a series of periodic examinations. This system detects very small lumps and allows easy, accurate, monitoring of suspicious areas over an extended time period.

17 Claims, 4 Drawing Sheets

APPARATUS FOR DETECTING VERY SMALL BREAST ANOMALIES

FIELD OF THE INVENTION

This invention relates to apparatus and methods for detecting very small anomalous masses, in particular tumors, in the human breast.

BACKGROUND OF THE INVENTION

Recent findings indicate that one of eight women will develop breast cancer, the second leading cause of cancer death in women. Unopposed estrogen activity is an important pathogenic factor, with other risk factors including nulliparity, early menarche, late menopause, a family history of breast cancer, middle age and prior breast cancer.

The earliest indication of breast cancer generally is the occurrence of a painless lump, sometimes associated with nipple discharge and skin retraction. Later symptoms are generally due to metastases to bone, brain, lungs and liver. Early diagnosis may be possible through monthly self-examinations. Mammography has proven beneficial in early detection.

When a very small lump, <2 cm, is detected, a biopsy is generally performed, followed by treatment when the lump is found to be malignant. This can range from a lumpectomy with possible radiation treatment of axillary nodes to a modified radical mastectomy with axillary node dissection. With early treatment, the five-year survival rate is about 85%. Without early detection, if distant metastasis occur, the survival rate may drop to 10% or less.

Early detection of lumps is thus essential. Monthly self-examinations are very desirable, followed by examination by a physician if any suspicious areas are detected. It is, however, difficult for an unskilled person to detect very small lumps or to do a thorough examination.

Periodic palpation of the breasts by a physician and mammography will often detect very small tumors. These examinations should be reasonably frequent, particularly in older women, in order to detect tumors before they can metastasize. However the cost of frequent examinations, plus the accumulated radiation exposure from frequent mammograms tend to limit frequency. In addition, mammography may miss very small tumors, especially in the dense breasts of younger women. Further, pregnant women should avoid exposure to radiation.

Thus, there is a continuing need for improved methods and apparatus for very early detection of very small breast lumps that could be malignant, while avoiding radiation exposure.

SUMMARY OF THE INVENTION

The above-noted problems, and others, are overcome in accordance with this invention by an apparatus for thoroughly palpating entire breasts in a continuous, automatic scanning manner, to detect changes in breast tissue physical characteristics such as tissue density, surface color the tissue, tissue temperature and, where anomalies are detected, mobility and size of the anomaly.

The overall system includes a bed upon which the patient lies face up and which includes means for precisely positioning the patient in the same position for each of a series of periodic examinations. A detection head is mounted on a carriage for movement in three dimensions adjacent to a patient on the bed. A locator head associated with the detection head controls the bed positioning means to position the breasts in precisely the same position as for prior examinations. A palpation means on the detection head includes a finger-like palpation end movable toward and away from the breast surface to palpate the breast in the same general manner as a physician. The palpation device is preferably mounted so as to be movable across the entire breast surface sequentially while maintaining the finger generally perpendicular to the breast surface.

Information sensed by the palpation device and position information from the detection head and palpation means are collected, stored and displayed in a conventional manner, such as is done with information from other systems such as computerized tomography and magnetic resonance imaging. The display will reveal any anomalies detected, so that further testing, such as through a biopsy, can be done.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
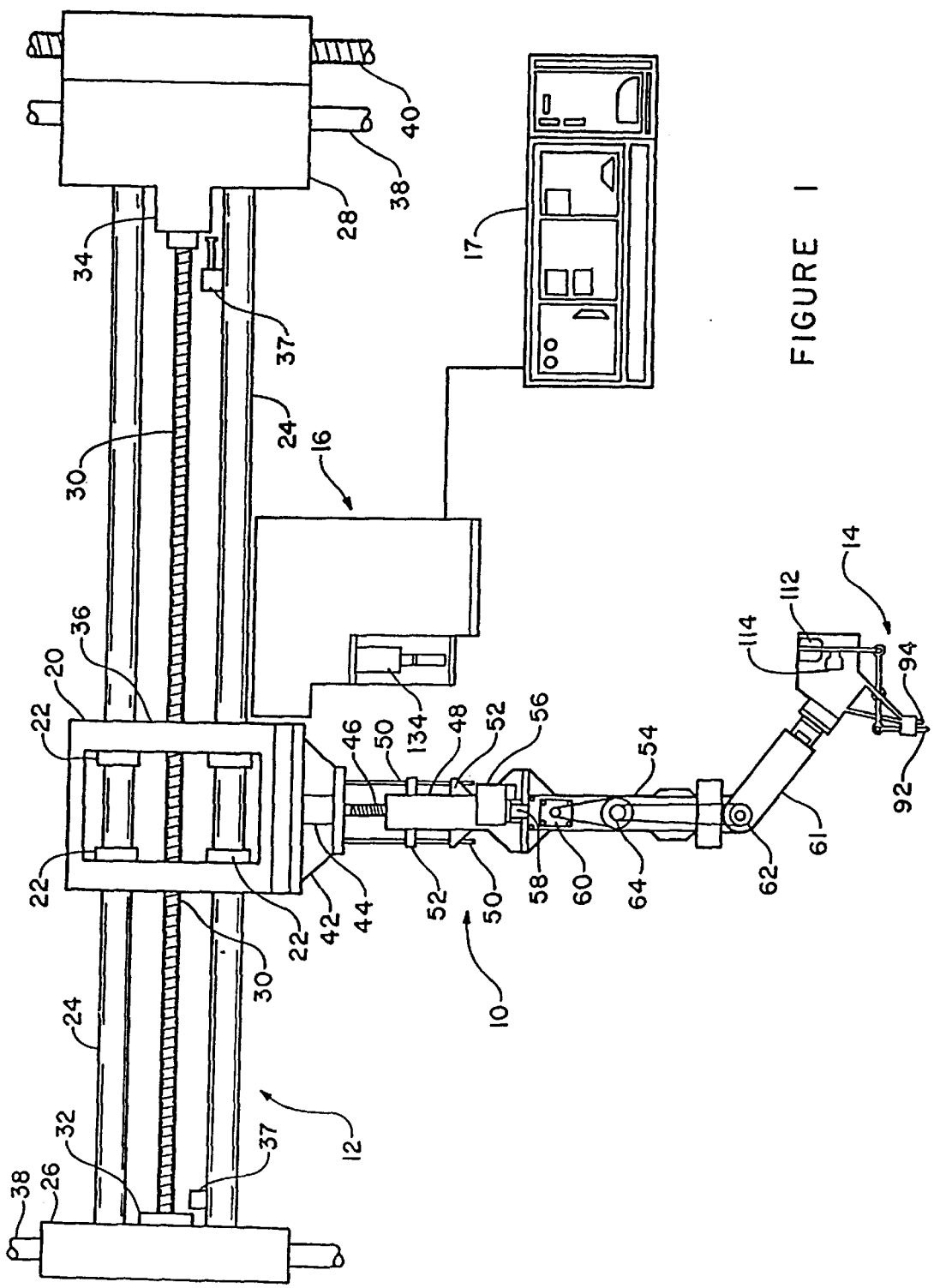
FIG. 1 is a schematic elevation view of the entire anomaly detection apparatus.

Referring to FIG. 1 there is seen a carriage 10 mounted at a proximal end on a horizontal support 12 for movement therealong a detection head 14 (as detailed in FIGS. 3 and 4) is mounted at the distal end of carriage 10. A locator head 16 (detailed in FIG. 5) is mounted to detection head 14 for movement therewith. Digital information from and to detection head 14, locator head 16 and control commands to the various motors, limit switches and the like is passed between a computer center 17 as schematically indicated. Information will be received, stored, interpreted and displayed in the same manner as other medical scanning devices, such as CAT scans, MRI scans, etc. Three dimensional images can be viewed on a conventional computer monitor. If desired, images may be shown with different tissue density areas shown in different colors. Artificial intelligence techniques may be used to improve system performance. The combination of tissue density information as developed by palipatation and the ancillary local color and temperature information results in detection of much smaller tumors and the ability to easily track changes in discrete tissue areas.

Horizontal support 12 is mounted on a vertical support mechanism 18 (as detailed in FIG. 6) along which support 12 can move in a vertical direction. Horizontal support includes a traveler 20 that rides in bearings 22 along rods or tubes 24 that are secured at their ends to end blocks 26 and 28. A lead screw 30 extends from a bearing 32 at end block 26 to a drive motor 34 at end block 28. Lead screw 30 extends trough correspondingly threaded openings in walls 36 of traveler 20 so that traveler 20 will move to the right or left as the lead screw is rotated in one direction or the other. Conventional limit switches 37 prevent overtravel of traveler 20.

Guide rods 38 extend vertically through end blocks 26 and 28 and a lead screw 40 extends vertically through end block 28. These components are shown completely and discussed in conjunction with the discussion of FIG. 6, below.

Carriage 10 includes a base 42 secured to traveler 20. A motor 44 within base 42 rotates a screw 46 that is threaded into an intermediate body 48 to raise and lower that body as the screw is rotated one way or the other. A pair of guide rods 50 extend through brackets 52 to guide movement of body 48. A lower body 54 is secured to intermediate body 48 for rotation relative thereto. A motor 56 is mounted on intermediate body 48 with lower body 54 mounted on the motor shaft 56 for rotation with the shaft.

An arm 61 is pivotally mounted at pivot 62 on bracket 64 mounted on the distal end of lower body 54. A motor 60 on lower body 54 drives a pulley 62 on arm 61 through a jackshaft 64.

Figure 6:
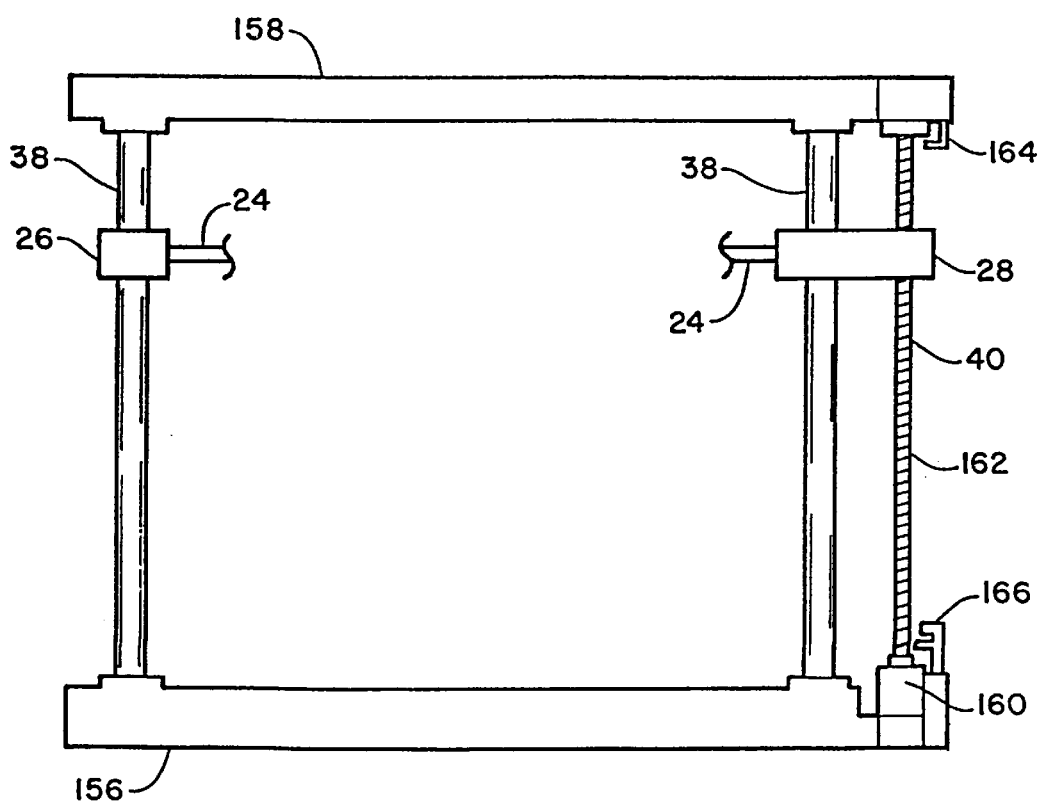
FIG. 6 is a schematic elevation view of the vertical positioning mechanism of the anomaly detection apparatus.

Thus, the entire carriage can be moved horizontally by horizontal support 12 and vertically by the vertical support of FIG. 6. Lower body 54 of the carriage can be rotated through a full circle. Arm 61 carrying detection head 14 can be pivoted through at least 180°. This combination of movements permits detection head to be positioned in any desired position relative to any portion of a breast surface.

Figure 2:
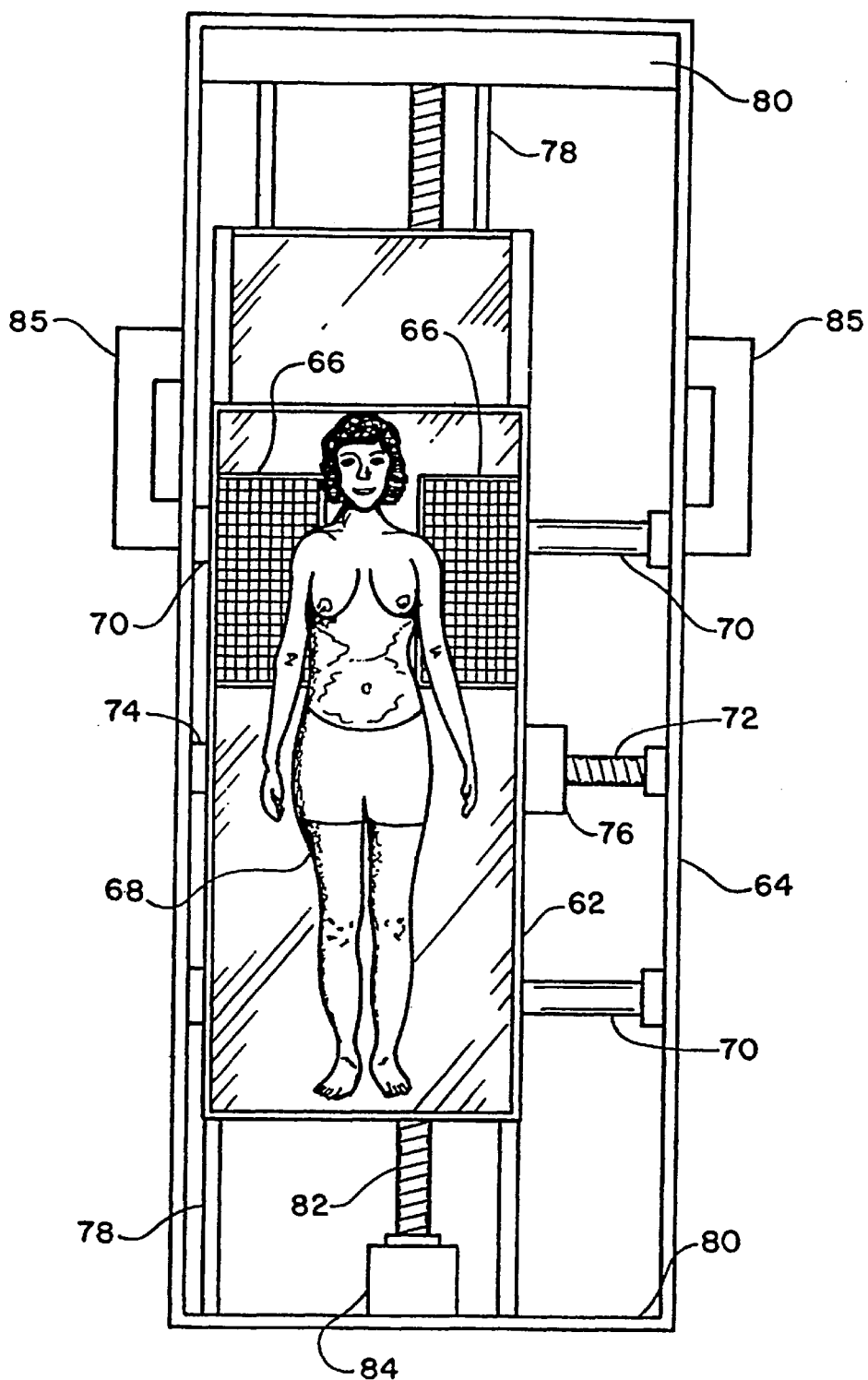
FIG. 2 is a schematic plan view showing a patient positioned on the patient positioning bed.

In order to perform a complete breast examination, a person lies face-up on a bed 62 mounted on a position adjusting assembly 64 as seen in FIG. 2. The bed will be positioned generally below detection head 14 of FIG. 1.

Bed 62 has a comfortably padded upper surface, with matrix boards 66 adjacent to the shoulders of person 68. Conventional optical measuring means (not shown) can be provided to locate the exact positin of arms, shoulders and neck relative to the matrix board pattern during a first examination. Then, when the person 68 is again postioned on the bed 62 for a later examination, the optical system in conjunction with conventional software can again detrermine the person's position relative to matrix boards 66 and the position of the bed can be adjusted in accordance with stored location information to place the person in substantially the identical position as for the first examination. Further, if person 68 were to move during the examination, the optical system can detect and correct for the change in position. It is highly desirable that the person be positioned as identically as possible for each of the periodic examinations.

The underside of bed 62 includes conventional tubular bearings (not seen) through which horizontal guide rods 70 pass. A central threaded rod 72 engages end bearings 74 on assembly and passes through a conventional motor driven nut assembly 76. As the motor driven nut assembly is rotated in one direction or the other, bed 62 will be correspondingly moved sideways. Similarly, a pair of guide rods 78 extend between end walls 80 of assembly 64. Guide rods 70 and 78 are each arranged in a set of at least two parallel guide rods. A central threaded rod 82 passes through a conventional threaded block (not seen) secured to the underside of bed 62. A motor 84 rotates threaded rod 82 to move the bed in either lengthwise direction, as desired. The overhead end blocks 26 and 28 (FIG. 1) are mounted on posts 85, the lower portions of which are seen in FIG. 2.

Figure 3:
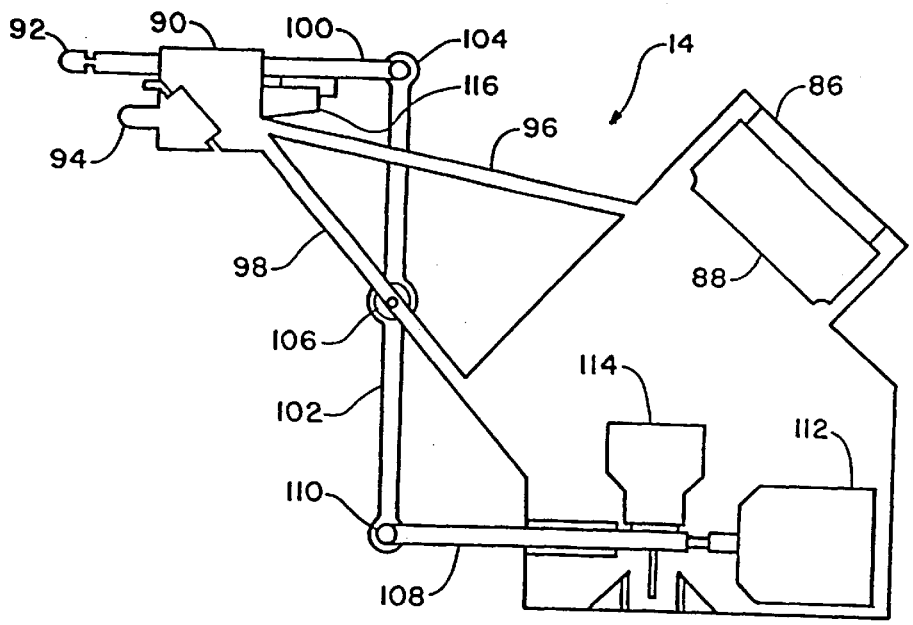
FIG. 3 is a schematic elevation view of the detection head actuator.

The operating structure of detection head 14 is detailed in schematic elevation view in FIG. 3. A removable connection 86 for main housing 87 mounting detection head 14 on arm 61. Preferably, detection head 14 is rotatable relative to arm 61 by a motor 88.

A detector housing 90 for palipatation finger 92 and sensor 94 for sensing distance, color and temperature is mounted on main housing 87 through arms 96 and 98. Finger 92 is designed to act like a physician's palpating finger in a manual breast examination. Typically, finger 92 will be formed from a sturdy, disposable material, such as glass.

Sensor 94 includes a distance measuring mechanism, of the sort used in cameras and the like, for providing precise distances between the breast surface and the sensor. If desired a plurality of spaced range finders, such as the range finder conventional schematically indicated at 95, may be used to assure that palipatation finger 92 is oriented perpendicular to the breast surface.

A conventional means for measuring the color of the breast surface being examined is included in sensor 94. Typically, this can be a conventional prism for breaking up incoming light and refracting each color of light to an independent photo electric or photo resistive sensor.

Palipatation finger 92 is secured to the distal end of an shaft 100 that is slidable through housing 90 and pivoted at proximal end to the distal end of arm 102 at pivot point 104. Arm 102 is rotatable about an axis 106 centrally located along arm 98. The proximal end of arm 102 is pivotally connected to drive shaft 108 at pivot point 110. When shaft 108 is moved axially by an actuator within actuator housing 112 (as detailed below in conjunction with the description of FIG. 4) shaft 100 and palipatation finger move a proportional distance in the opposite direction. As discussed below, a laser reader in reader housing 114 detects movement of shaft 108 and the feedback resistance to movement experienced by palipatation finger 92 when pressing against breast tissue.

An error correction sensor 116 is provided on housing 90, cooperating with a member 119 mounted on shaft 108 to detect and correct positioning errors. It is possible that the moving components of the detection head mechanism shown in FIG. 3 may not be positioned correctly any time after coils 118 (FIG. 4) have been activated and repositioned. Resetting the position of the moving parts, e.g., detection head 90, shaft 100, arm 102, and therefore palpation finger 92, is accomplished by the first coil 118 at the left as seen in FIG. 4. Slight changes in position of the breast skin, due to breathing or the like, is sensed by finger 92 and a corresponding position correction signal is sent to the leftmost coil 118 to correct for that displacement. While this precision is often not required, it is available if needed.

The internal components within actuator housing 112 and reader housing 114 are schematically illustrated in FIG. 4. A series of electromagnetic coils 118 are arranged in a uniformly spaced relationship along a central tube 120. An end shaft 122 is axially secured to the proximal end of shaft 108 and extends into tube 120. Shaft 108 slides in a sleeve 123.

End shaft 122 is formed from a magnetic material so that when coils 118 are actuated sequentially, beginning with the coil adjacent to the end of shaft 122 fastened to shaft 108 the magnetic forces will tend to pull end shaft 122 into tube 120. As seen in FIG. 2, this pulls shaft 108, rotating arm 102 and extending shaft 100 and pressing palipatation finger 92 toward an adjacent breast.

The magnetic forces provide a rather "soft" pull so that breast tissue can stop the advance of palipatation finger 92 without severe compression. The distance the finger advances will be in proportion to the density of the tissue, with a lump of more dense tissue resisting penetration, so the distance the finger advances will be less. This arrangement of arm 102, shafts 100 and 108 with magnetic coils 118 could be thought of as a weighing scale where breast tissue density corresponds to the object to be weighed and the magnetic actuator is the standard portion of weight placed on the other side of the scale.

In operation, the first coil 118 will be actuated, moving palpation finger 92 a predetermined distance. Typically the coil is powered up stepwise, at about 250 mv per step up to about 10 volts maximum. The pressure change per step is typically only around about 10 grams per $mm^2$ per step. If tissue resistance is low, the second coil 118, and others in sequence, will be similarly actuated, further moving the finger. Eventually, tissue resistance will reach a predetermined level and the distance traveled by the finger will be measured, as detailed below, and the information transferred to conventional information storage means.

The mechanism for encoding and transmitting the palpation information to the storage and use station is enclosed in reader housing 114. As seen in FIG. 4, a conventional laser optic card 124, using technology as applied in musical compact disks but with a single straight track, is carried by shaft 108. A laser card reader 126 reads the shaft position from the card 124 and transmits the encoded information to the information collection station. There, the information can be converted to machine language or any desired format for interpretation by conventional software systems of the sort used in CAT scan systems or other medical scanning systems. Any error or mechanical tilt is detected in real time by error correction sensor 116 that filters out any mechanical movement other than the desired palpation movement.

Figure 4A:
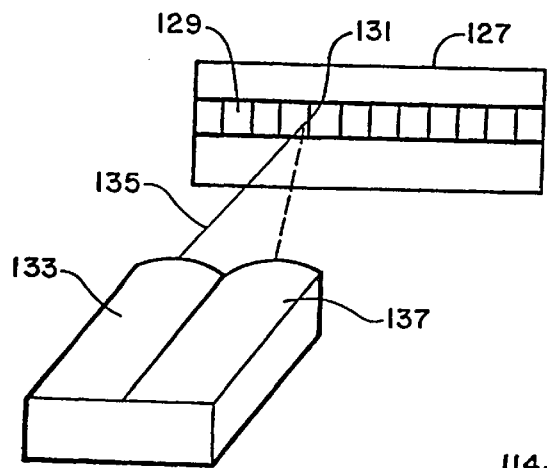
FIG. 4 is a schematic elevation view of the detection head positioning means.
Figure 4:
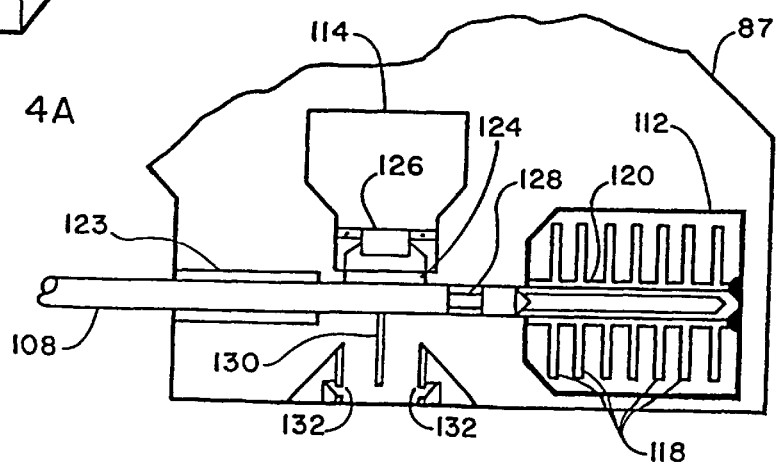

A typical laser card 127 of the sort used in reader 126 is schematically illustrated in FIG. 4a. Card 127 is similar to a compact disk, having a series of reflecting areas 129 separated by non-reflective areas 131. While non-reflecting areas 131 could be light absorbing, generally it is preferred that they be transparent so the impacting light will be passed through. A laser transmitter 133 directs a laser beam 135 against the patterned area of laser card 126. When the laser beam 135 hits a reflecting area, reflected light is picked up by a receiver 137. As card 127 is moved transversely, conventional software can count the pattern of reflection pulses to measure movement of shaft 106 and, ultimately, palpation finger 92. The reflecting areas can be as small as about 0.001 mm for highly precise movement measurement.

An adjustment mechanism 128, such as a threaded adjustment shaft acting similar to a turnbuckle, is provided to adjust the position of arm 108 relative to the array of electromagnet coils 118. The maximum excursion of arm 108 is limited by pin 130 extending from shaft 108 and limit switches 132 The unit will thus sequentially test areas to provide a "picture" of the entire breast surface, revealing density changes indicative of tumors on a very fine scale, in a manner similar to the images produced in MRI, CAT and other physical scanning methods.

Figure 5:
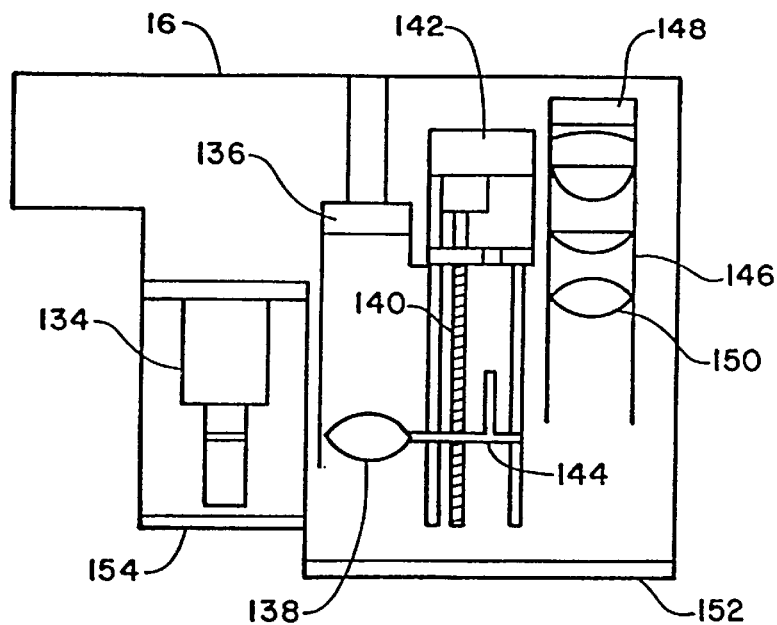
FIG. 5 is a schematic diagram of the locator head assembly.

To provide the maximum consistency of results from one examination to the next, it is highly desirable that the person and the breasts be positioned as identically as possible for each examination. The movable bed arrangement shown in FIG. 2 aids, in cooperation with. Locator head 16 schematically illustrated in FIG. 5, provide accurate positioning by locating the position of a person on the bed and actuating the various carriage, bed and detection head movement mechanisms under computer control to locate the breast to be examined in substantially the same position it was in at the last prior examination.

A digital camera 134 provides a digitized image of the breast and patient in a matrix manner to supply sufficient data for the ongoing examination session and the preposition of the patient whenever a new image is required. A computer system can compare the original image to a subsequent image at the start of a subsequent examination so that the patient's position can be adjusted until the images match.

A white light source 136 is provided with a schematically illustrated focussing lens system including lens 138, a lead screw 140 rotatable by motor 142 and threaded through a lens mount bracket 144 to focus a light spot on the breast surface. As the spot of light is moved transversely and focussed at different depths along the present, the scan can be saved in computer memory in a conventional manner to produce a three-dimensional image of the breast.

In addition, a laser scanner 146, including a laser emitter 148 and a focussing system 150 for producing a small spot on the breast being examined may be used in the same way as the white light spot to create a three-dimensional image. Typically, a 680–820 mm, 0.0095 mw laser may be used, since that laser has sufficient power for imaging without damaging the skin.

A window 152 of glass or plastic that is transparent to the white light and laser light closes the bottom of locator head 16. A similar window 154 covers the side of head 16 adjacent to camera 134.

The mechanism for raising and lowering the entire carriage 10 as seen in FIG. 1 is illustrated in FIG. 6. Vertical guide rods 38 extend from a sturdy base 156 to a top plate 158. End blocks 26 and 28 carry horizontal support 12 (FIG. 1, omitted from this Figure for clarity) for vertical movement therealong.

A powerful motor 160 rotates a sturdy lead screw 162 threaded through block 28. An upper limit switch 164 and a lower limit switch 166 prevent movement of horizontal support beyond desired limits. For a very strong, sturdy assembly, base 156 will rest on the floor or a sub-floor so that bed assembly 64 could be positioned within the frame formed by base 156, top support 158 and guide rods 38.

The image produced by either of these light spots produced at a first examination can be compared to an initial image produced at a later examination to adjust the breast position to substantially match the original position. This will aid in re-examining a suspicious spot or lump found in the initial examination during later examinations.

The three-dimensional images can be divided into a matrix of cubes or slices with geometric indicia (e.g., a cube might be identified as cube, 2,4,9 on an x-y-z axis basis) and locations can be directly compared between the light spot image and the finger palpation locations.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. Apparatus for detecting anomalies in breast tissue which comprises:
   a movable carriage;
   a detection head mounted on said carriage for movement therewith;
   a palpation finger mounted on said detection head for movement relative to said detection head along a line;
   means for moving said palpation finger along said line into pressure contact with breast surface;

means for measuring and recording the extent of penetration of said palpation finger into breast surface corresponding to a predetermined force extending said finger;

means for pivoting said detection head about a first axis;

means for rotating said detection head about a second axis; and means for moving said carriage in at least one direction.

2. The apparatus according to claim 1 further including a locator head mounted on said carriage, said locator head including means for imaging a breast and positioning said palpation finger at predetermined locations relative to said breast surface.

3. The apparatus according to claim 2 wherein said locator head includes a digital camera for providing an image of a breast located adjacent to said locator head.

4. The apparatus according to claim 2 wherein said locator head includes a white light source and optical means for focusing light from said white light source on a spot on a breast adjacent to said locator head.

5. The apparatus according to claim 2 wherein said locator head includes a laser light source and optical means for focusing light from said laser light source on a spot on abreast adjacent to said locator head.

6. The apparatus according to claim 1 further including means for orienting said line of movement of said palpation finger generally perpendicular to any point on said breast surface.

7. The apparatus according to claim 1 further including sensor means mounted on said detection head adjacent to said palpation finger for measuring at least one of breast surface color and temperature over a predetermined area.

8. The apparatus according to claim 1 further including a bed assembly for supporting a person adjacent to said detection head, said bed assembly including a body supporting bed panel moveable in two relatively perpendicular directions in a horizontal plane.

9. The apparatus according to claim 8 wherein said bed panel is mounted on at least one guide rod set for movement of said bed panel therealong in each of said two relatively perpendicular directions and at least one lead screw is operatively connected parallel to each guide rod set to move said bed panel along each said guide rod set.

10. The apparatus according to claim 1 wherein said apparatus further includes means for supporting said carriage for movement in two relatively perpendicular directions.

11. The apparatus according to claim 10 wherein said support means includes two parallel horizontal guide rods, a traveler mounted on said guide rods for movement therealong and a lead screw mounted parallel to said guide rods and engaging said traveler for moving said traveler along said guide rods.

12. A detection system for detecting anomalies in breast tissue which comprises:

a detection head housing;

a palpation finger mounted on said housing for movement relative to said detection head along a line;

means for moving said palpation finger along said line into pressure contact with a breast surface;

means for measuring and recording the extent of penetration of said palpation finger into breast surface corresponding to a predetermined force extending said finger;

means for pivoting said detection head housing about a first axis; and means for rotating said detection head housing about a second axis.

13. The detection system according to claim 12 further including means for orienting the movement of said palpation finger substantially perpendicular to any point on said breast surface.

14. The detection system according to claim 12 further including sensor means mounted on said detection head adjacent to said palpation finger for measuring at least one of breast surface color and temperature over a predetermined area.

15. Apparatus for detecting anomalies in breast tissue which comprises:

horizontal support means;

a movable carriage mounted on said horizontal support means for movement in a horizontal direction;

a detection head mounted on said carriage for movement therewith;

a palpation finger mounted on said detection head for movement relative to said detection head along a line;

means for moving said palpation finger along said line into pressure contact with breast surface;

means for orienting said palpation finger so that said line is substantially perpendicular to said breast surface;

means for measuring and recording the extent of penetration of said palpation finger into breast surface corresponding to a predetermined force extending said finger;

means for pivoting said detection head about a first axis;

means for rotating said detection head about a second axis;

a locator head mounted on said carriage, said locator head including means for imaging a breast and positioning said palpation finger at predetermined locations relative to said breast surface;

said locator head includes a light source and optical means for focussing light from said white light source on a spot on a breast adjacent to said locator head; and sensor means mounted on said detection head adjacent to said palpation finger for measuring at least one of breast surface color and temperature over a predetermined area.

16. The apparatus according to claim 15 further including a bed assembly for supporting a person adjacent to said detection head, said bed assembly including a body supporting bed panel moveable in two relatively perpendicular directions in a horizontal plane.

17. The apparatus according to claim 16 wherein said bed panel is mounted on at least one guide rod set for movement of said bed panel therealong in each of said two relatively perpendicular directions and at least one lead screw is operatively connected parallel to each guide rod set to move said bed panel along each said guide rod set.

\* \* \* \* \*